US009223298B2

(12) United States Patent
Phillips et al.

(10) Patent No.: US 9,223,298 B2
(45) Date of Patent: *Dec. 29, 2015

(54) BIOMETRIC IDENTIFICATION SYSTEM USING PULSE WAVEFORM

(71) Applicant: Integrated Monitoring Systems, LLC, Lakewood, CO (US)

(72) Inventors: Brian K. Phillips, Lakewood, CO (US); Geoffrey A. Wilson, Roseburg, OR (US)

(73) Assignee: Integrated Monitoring Systems, LLC, Lakewood, CO (US)

( * ) Notice: Subject to any disclaimer, the term of this patent is extended or adjusted under 35 U.S.C. 154(b) by 306 days.

This patent is subject to a terminal disclaimer.

(21) Appl. No.: 13/916,818

(22) Filed: Jun. 13, 2013

(65) Prior Publication Data

US 2013/0271263 A1    Oct. 17, 2013

Related U.S. Application Data

(63) Continuation-in-part of application No. 13/079,219, filed on Apr. 4, 2011, now Pat. No. 8,773,239, and a continuation-in-part of application No. 13/739,224, filed on Jan. 11, 2013.

(51) Int. Cl.
  *G05B 1/00* (2006.01)
  *A61B 5/117* (2006.01)
  (Continued)

(52) U.S. Cl.
  CPC . *G05B 1/00* (2013.01); *A61B 5/117* (2013.01); *A61B 5/021* (2013.01); *A61B 5/026* (2013.01); *A61B 5/14551* (2013.01)

(58) Field of Classification Search
  USPC ...................................................... 340/5.82
  See application file for complete search history.

(56) References Cited

U.S. PATENT DOCUMENTS 5,220,919 A    6/1993  Phillips et al.
5,719,950 A    2/1998  Osten et al.
(Continued)

FOREIGN PATENT DOCUMENTS

WO      94/07407        4/1994
WO   2012/138663 A2    10/2012

OTHER PUBLICATIONS

PCT International Search Report and Written Opinion for International Application No. PCT/US2012/032014, dated Jul. 27, 2012, 10 pages.

(Continued)

*Primary Examiner* — Brian Zimmerman
*Assistant Examiner* — Bhavin M Patel
(74) *Attorney, Agent, or Firm* — Dorr, Carson & Birney, PC

(57) ABSTRACT

A biometric identity confirmation system is based on pulse waveform data for the subject. During an initial enrollment mode, pulse waveform data for a known subject are used to generate subject characterization data for the known subject. The subject characterization data includes an exemplar created by synchronous averaging of pulse waveform data over multiple pulse cycles. A number of trigger candidate are identified for the start point of each pulse cycle. The time delay between trigger candidates is analyzed to discard false trigger candidate and identify true candidates, which are then used as the start points for each pulse cycle in synchronous averaging of the pulse waveform data. During a subsequent identity authentication mode, pulse waveform data for a test subject are analyzed using the subject characterization data to confirm whether the identity of the test subject matches the known subject.

11 Claims, 7 Drawing Sheets

(51) Int. Cl.
  *A61B 5/021* (2006.01)
  *A61B 5/026* (2006.01)
  *A61B 5/1455* (2006.01)

(56) References Cited

U.S. PATENT DOCUMENTS

| | | | |
|---|---|---|---|
| 6,483,929 | B1 | 11/2002 | Murakami et al. |
| 6,985,070 | B1 | 1/2006 | Parker |
| 6,993,378 | B2 | 1/2006 | Wiederhold et al. |
| 7,002,477 | B1 | 2/2006 | Camhi |
| 7,388,493 | B2 | 6/2008 | Lerch et al. |
| 7,441,123 | B2 | 10/2008 | Grant et al. |
| 7,536,557 | B2 | 5/2009 | Murakami et al. |
| 7,603,887 | B2 | 10/2009 | Schlichte |
| 7,611,461 | B2 | 11/2009 | Hawthorne et al. |
| 7,616,123 | B2 | 11/2009 | Ridder et al. |
| 7,641,611 | B2 | 1/2010 | Hawthorne et al. |
| 7,724,925 | B2 * | 5/2010 | Shepard .................... 382/115 |
| 7,756,558 | B2 | 7/2010 | Ridder et al. |
| 7,796,013 | B2 | 9/2010 | Murakami et al. |
| 2003/0135097 | A1 * | 7/2003 | Wiederhold et al. .......... 600/301 |
| 2004/0236199 | A1 | 11/2004 | Hawthorne et al. |
| 2004/0239510 | A1 | 12/2004 | Karsten |
| 2006/0013445 | A1 | 1/2006 | Lange |
| 2006/0074300 | A1 * | 4/2006 | Green ........................ 600/427 |
| 2007/0177770 | A1 | 8/2007 | Derchak et al. |
| 2010/0108425 | A1 | 5/2010 | Crespo et al. |
| 2011/0066041 | A1 * | 3/2011 | Pandia et al. ................. 600/484 |

OTHER PUBLICATIONS

PCT Written Opinion of the International Searching Authority for International Application No. PCT/US2014/041004, dated Apr. 13, 2015, 4 pages.

* cited by examiner

*Enrollment Mode*

*Authenticate Identity Mode*

BIOMETRIC IDENTIFICATION SYSTEM USING PULSE WAVEFORM

RELATED APPLICATIONS

The present application is a continuation-in-part of the Applicants' co-pending U.S. patent application Ser. No. 13/079,219, "entitled "Biometric Identification System Using Pulse Waveform," filed on Apr. 4, 2011. The present application is also a continuation-in-part of the Applicants' co-pending U.S. patent application Ser. No. 13/739,224, entitled "System for Biometric Identity Confirmation," filed on Jan. 11, 2013, which claims priority to U.S. Provisional patent application 61/589,084, filed on Jan. 20, 2012.

BACKGROUND OF THE INVENTION

1. Field of the Invention

The present invention relates generally to the field of biometric identity confirmation. More specifically, the present invention discloses a system for biometric identity confirmation based on analysis of pulse waveform data for a test subject.

2. Background of the Invention

Biometric identification is the process of recognizing or rejecting an unknown person as a particular member of a previously characterized set, based on biological measurements. The ideal biometric characterization is specific to the individual, difficult to counterfeit, robust to metabolic fluctuations, insensitive to external conditions, easily measured, and quickly processed.

Fingerprint, retinal, iris, and facial scans are well-known biometric identification techniques relying on image processing. Images are two-dimensional, requiring sophisticated and computationally intensive algorithms, the analysis of which is often complicated by random orientation and variable scaling. Voice recognition is an example of biometric identification amenable to time series analysis, an inherently simpler one-dimensional process.

The simplest biometric identifiers can be expressed as a single parameter, such as height or weight. Single parameter identifiers have been the only quantitative means of identification throughout most of history. The price of simplicity is the loss of specificity, and in the case of weight, the lack of constancy over time. Nevertheless, single-parameter biometrics remain effective identifying factors, as is obvious from their continued use.

Identity tracking/confirmation is the process of following the whereabouts of a known subject moving unpredictably among similar individuals, perhaps with deceptive intent. Tracking/confirmation is somewhat simpler than identification, because it merely requires distinguishing the subject from all others rather than distinguishing every individual from every other, and because continuous rather than episodic data are available. Biometric identity tracking/confirmation is the continuous verification that a body-mounted sensor has remained on the subject, and has not been surreptitiously transferred to an impostor. For the purposes of this application, the term "biometric identification" should be broadly construed to encompass both biometric identification in its narrower sense, as described above, and identity tracking/confirmation.

SUMMARY OF THE INVENTION

This invention provides a system for biometric identity confirmation based on pulse waveform data for the test subject. During an initial enrollment mode, pulse waveform data for a known subject are used to generate subject characterization data for the known subject. The subject characterization data includes an exemplar created by synchronous averaging of pulse waveform data over multiple pulse cycles. A number of trigger candidate are identified for the start point of each pulse cycle. The time delay between trigger candidates is analyzed to discard false trigger candidate and identify true candidates, which are then used as the start points for each pulse cycle in synchronous averaging of the pulse waveform data. During a subsequent identity authentication mode, pulse waveform data for a test subject are analyzed using the subject characterization data to confirm whether the identity of the test subject matches the known subject.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

The present invention provides a biometric system for characterizing individuals by the non-invasive sensing of the subject's pulse waveform for the purposes of identification and identity tracking/confirmation. The major components include a computer processor, data storage, and a pulse sensor adjacent to the subject's tissue that generates time-series data based on the subject's pulse waveforms.

As an overview, the processor initially receives and analyzes the pulse waveform data from the pulse sensor for a known subject to generate subject characterization data identifying the known subject. Thereafter, in the identity authentication mode, the processor receives data from the pulse sensor for a test subject, who may or may not be the known subject. The processor analyzes this data in conjunction with the stored subject characterization data to determine whether the test subject is the same as the known subject. For the purposes of this application, it should be understood that the phrase "test subject" refers to the person whose identity is being tested or confirmed during the identity authentication mode of the present system.

Thus, the present system operates in one of two mutually exclusive modes—an enrollment mode and an identity authentication mode. The enrollment mode acquires subject data under the supervision of a trained technician, computes subject characteristics, calculates the probability of an impostor producing similar characteristics, and stores these findings in a client database for later use during the identity authentication mode.

Figure 1:
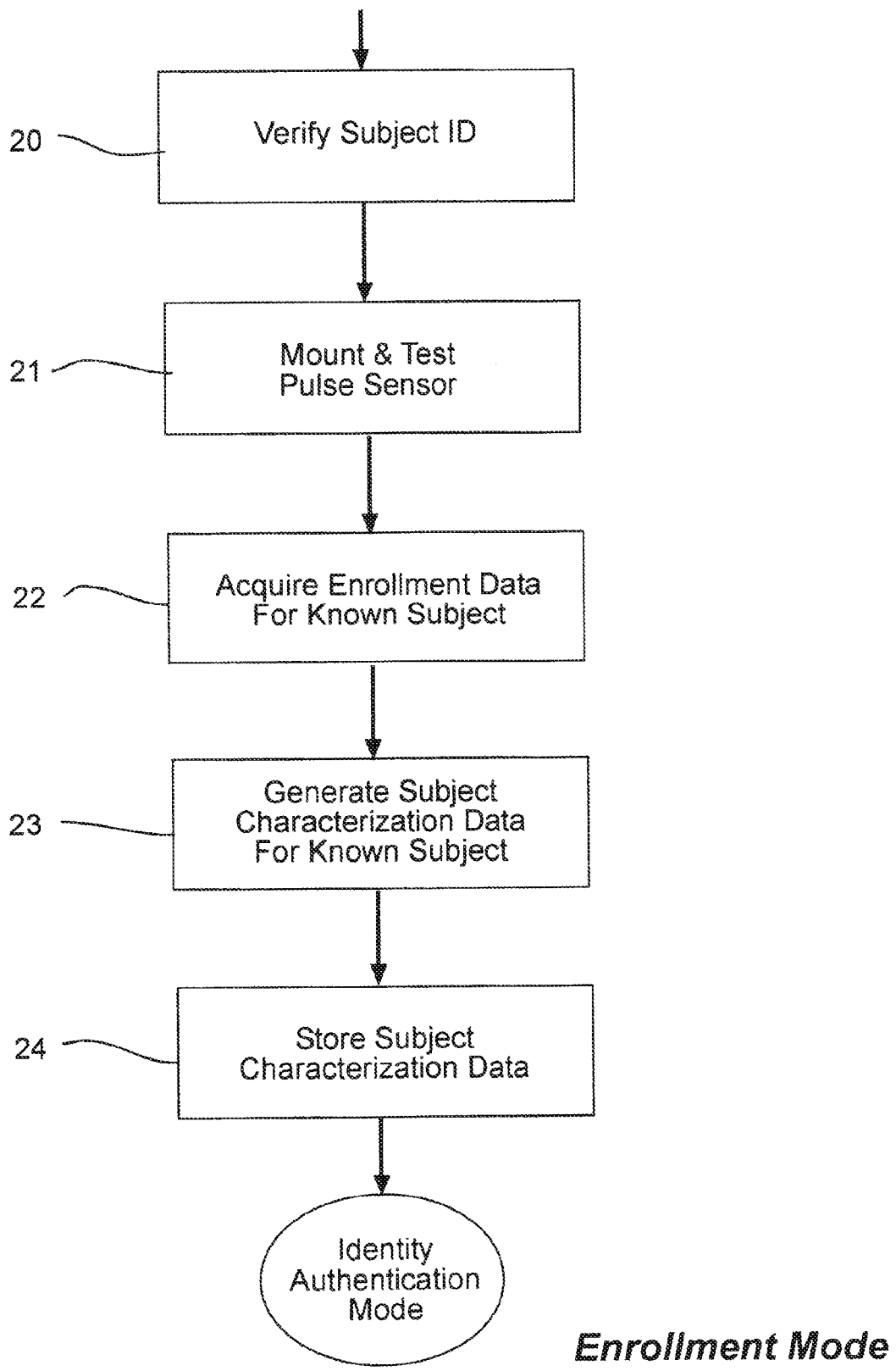
FIG. 1 is a flowchart of the enrollment mode of the present invention.

FIG. 1 is a general flowchart of the enrollment mode employed to initially build subject characterization data for a known subject. The operator first verifies the identity of the subject (step 20), and mounts and tests the pulse sensor on the subject (step 21). The processor acquires pulse waveform data from the pulse sensor for a brief period of time (step 22). The subject may be asked to undertake a range of activities to ensure the enrollment data are representative of that which may be encountered over the subject's normal day-to-day activities. The processor analyzes the enrollment data and generates subject characterization data for identifying the known subject (step 23). This subject characterization data is stored for later use during the identity authentication mode of the present system (step 24), as will be described below.

Figure 2:
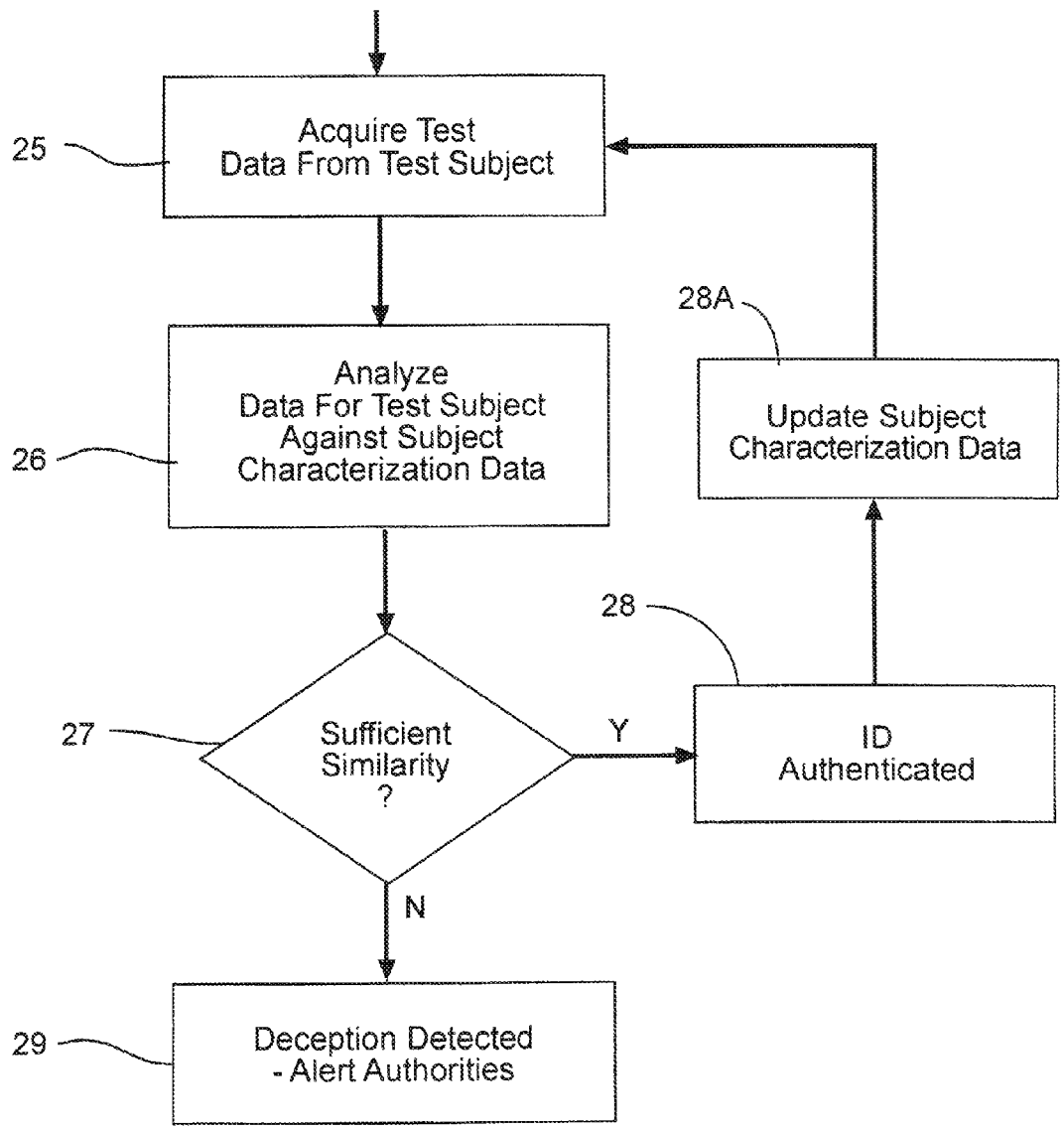
FIG. 2 is a flowchart of the identity authentication mode of the present invention.

The identity authentication mode is used to authenticate the identity of a test subject, who may or may not be the known subject from the enrollment mode. In this mode, the system acquires subject data unsupervised in the field, compares it to subject and impostor characteristics, and decides whether to authenticate or challenge identification. FIG. 2 is a flowchart of one possible embodiment of the identity authentication mode. For each identity authentication test, the processor acquires pulse waveform data from the pulse sensor for the test subject (step 25). The processor analyzes this test data using the subject characterization data (step 26). Based on this analysis, in step 27, the processor determines whether there is a sufficient degree of similarity between the pulse waveform characteristics of the known subject (from the subject characterization data) and the test subject to conclude that these subjects are the same person (step 28). If so, the processor may update the subject characterization data 18 to include the current test data (step 28A) and then loop back to step 25. Otherwise, if the processor determines that the current test subject is not the same as the known subject, an alarm can be activated to signal that deception has been detected (step 29).

As will be discussed below, the two modes in the preferred embodiment of the present invention share a common "acquire trial" procedure that acquires and pre-processes a short, contiguous time-series data of the digitized measurement, called a "trial".

Figure 3:
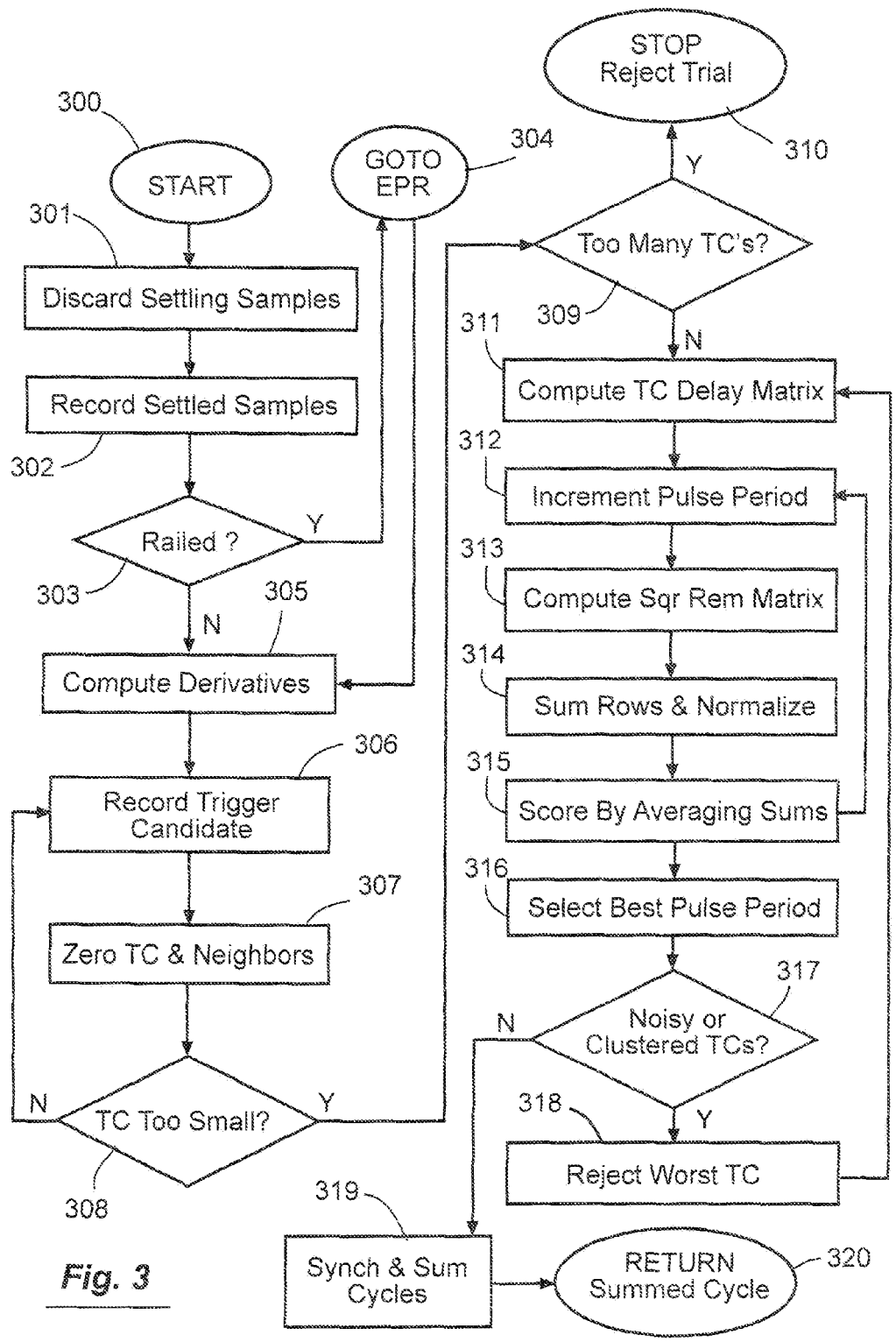
FIG. 3 is a flowchart of the "acquire trial" procedure.

FIG. 3 shows how the present system acquires a trial. The trial pulse waveform typically consists of a small number (e.g., ten) of pulse cycles, which are similar but not identical to each other. Performance is improved by synchronizing and summing pulse cycles to wash out noise. The goal of the procedure is to convert the multi-cycle waveform into a single representative cycle, or exemplar. Block 300 is the start of the procedure. Block 301 reads and discards pulse samples for a fixed duration (e.g., 1.5 seconds) while the waveform settles. After settling, block 302 reads and records samples for the remainder of the trial (e.g., 8.5 seconds).

Figure 7:
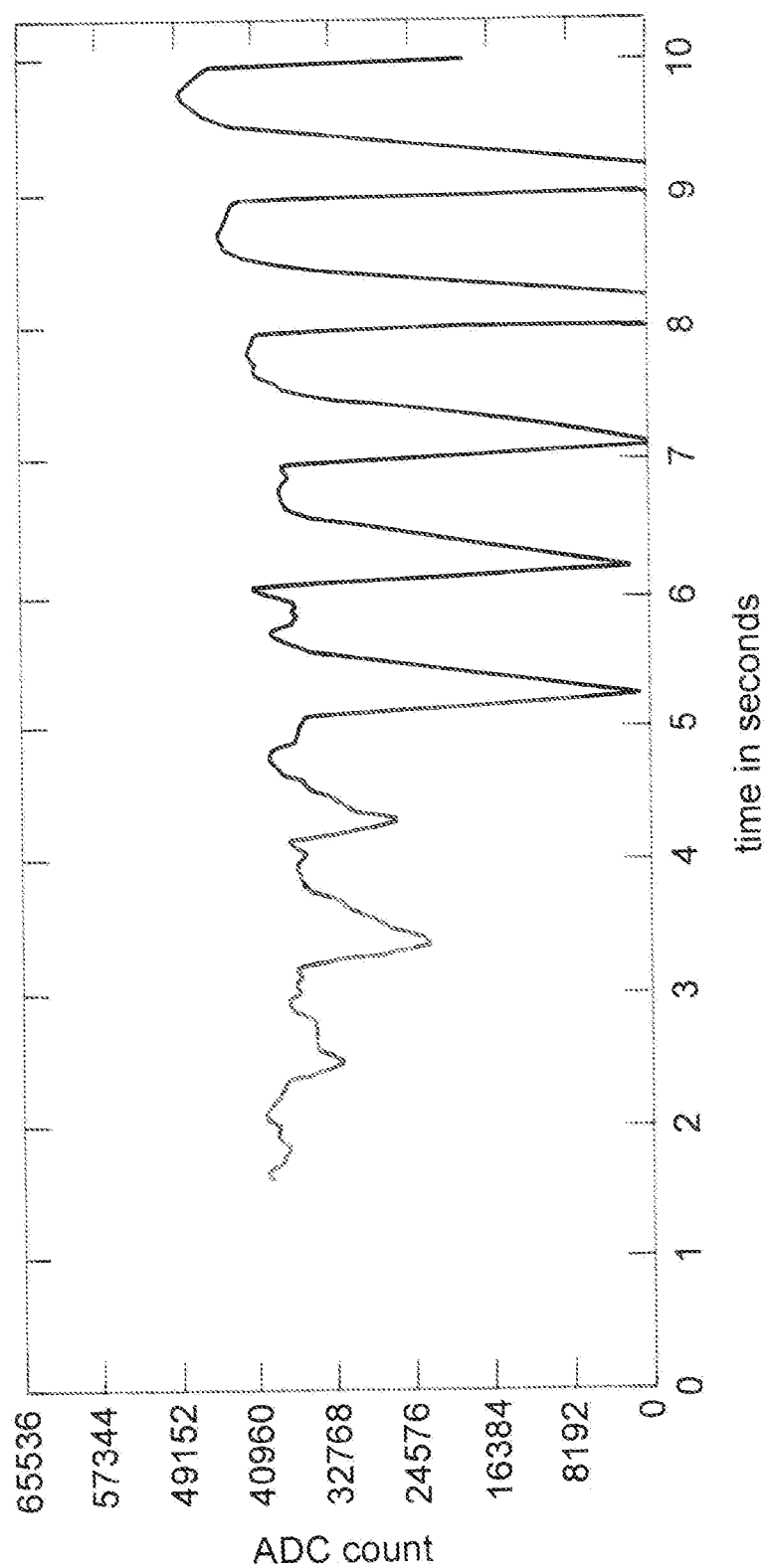
FIG. 7 is a graph showing an example of an enrollment trial with railed data.

Block 303 tests samples for "railing" (i.e., exceeding the limits of the digitizer, an indicator of trial corruption) as shown for example in FIG. 7. Upon detecting a railed sample, block 303 calls block 304, the extrapolative peak restoration routine, which is discussed below. If no recorded samples are railed, or railed peaks are reparable, control proceeds to block 305, which calculates the first and second derivatives of the pulse wave with respect to time, to eliminate baseline drift and generate triggers associated with the systolic excursion. Representing the subject's pulse wave with its first derivative also obscures the bio-informational nature of the signal, thus enhancing privacy. The derivatives may or may not be smoothed to reduce high frequency noise. Block 306 chooses the most negative excursion of the second derivative as the "trigger candidate" (TC). Next, block 307 zeroes the TC and some small number (e.g., four) of immediate predecessor and successor data, to avoid selecting the same peak again. Then, block 308 compares the present TC to the first TC. If the present TC is greater than some threshold fraction (e.g., ½) of the first TC, the procedure loops through blocks 306-308, acquiring another TC. If not, TC acquisition is deemed complete, and control proceeds to block 309. If there are many (e.g., eight) more TCs than can be accounted for according to the settled sampling time and maximum pulse rate (e.g., 17 for 8.5 seconds at 120 beats per minute), the sample is judged too noisy, and block 309 calls block 310, which rejects the trial and stops the procedure. If not, the trial is accepted, but some of the TCs may be noise spikes asynchronous to the underlying pulse cycle.

The section labeled as blocks 311-318 is called the "trigger sieve" because it removes asynchronous false triggers, thus enhancing performance. Block 311 calculates a square matrix of the delays $\Delta$ between every pair of TCs. Next, the procedure loops through all integer pulse periods, in units of the sampling period, from the fastest to the slowest measurable pulse (e.g., 50-150 for 100 Hz sampling and 120-40 beats per minute), to find the best fit to the preponderance of TCs. Block 312 increments the pulse period P. Block 313 computes the matrix of squared remainders $[\Delta \bmod P]^2$, where the "mod" operation yields the integer remainder with the smallest absolute value (e.g. 15 mod 8 equals −1, not 7). Block 314 sums the squared remainders for each TC relative to the other TCs, and normalizes such that a "score" near (much smaller than) unity indicates P is a poor (good) fit to the true pulse period. Block 315 averages the TC scores to evaluate P's goodness of fit. Block 316 selects the P with the lowest score. Next, block 317 detects if there are TCs with optimal-P scores greater than a preset threshold (e.g., 0.25), or any clustered TCs, as false triggers not synchronized with the prevailing pulsatile rhythm. If there is at least one false trigger, block 318 eliminates the TC with the largest optimal-P score, and control returns to block 311. If there are no false triggers, block 319 uses the true triggers to synchronize and sum the cycles, and block 320 returns the summed cycle to the calling program.

The following is a discussion of the procedure for extrapolative peak restoration (EPR) of clipped or railed pulse wave peaks in block 304. When prototyped, the prototype hardware appeared to have sufficient range to capture pulse wave data without overdriving the analog-to-digital convertor, or ADC. This is also known as clipping or railing. Subsequently, some strong-signal subjects have demonstrated pulse waves whose peaks are beyond the limits of the ADC, as shown for example in FIG. 7. One possible rule is to discard any trial that rails after initial settling, potentially resulting in much spoiled data. The alternative of reducing the sensitivity so that even the strongest pulses remain within bounds is unattractive because we also have several weak-signal subjects whose pulse wave can scarcely be discerned as it is. Therefore, we desire a method for the extrapolative restoration of the clipped pulse wave peaks.

FIG. 7 shows an example of the data used to develop this model. This represents about the worst trial that should be restored (any trial with worse railing should be discarded). Data from the initial settling (the first 1.5 seconds) is not shown. There are three clipped waves, with widths of 9, 22, and 19 consecutive ADC counts of zero respectively, for fifty total railed data. Clipping at the other rail 65535 is also possible, of course.

One embodiment of the present invention employs the following criteria: A railed trial should be restored if it has: (1) no clipped peak of width greater than 25; (2) tails sufficiently long for restoration on both sides of each clipped peak; and (3) has a total clipped width no greater than 85 (10% of the post-settling data). Otherwise, it should be discarded.

The method uses a Gaussian-weighted parabolic best fit. It marches through the data set, separately restoring each clipped peak in chronological order. One may as well specify fit window as wide as the exemplar (e.g. 49 data), and symmetrical about the mid-point of the railed segment of length L:

$$W(k) = \exp\left[-\frac{k^2}{2\sigma^2}\right]$$

for $|k|>\frac{1}{2}(L-1)$ if L is odd, and for $|k|>\frac{1}{2}L$ if L is even, and $W(k)=0$ for k otherwise; where (e.g. $k\in[-24,+24]$) is defined relative to the center-most datum if L is odd, and to the earlier member of the center-most pair of data if L is even; and $\sigma$ is a user-selected standard deviation (e.g., eight). The best fit $\tilde{Z}(k)=Ak^2+Bk+C$ is found by optimizing the fit coefficients using weighted least-squares. Because of symmetry, sums over odd powers of k vanish, yielding:

$$\begin{bmatrix} \Sigma Wk^4 & 0 & \Sigma Wk^2 \\ 0 & \Sigma Wk^2 & 0 \\ \Sigma Wk^2 & 0 & \Sigma W \end{bmatrix} \cdot \begin{bmatrix} A \\ B \\ C \end{bmatrix} = \begin{bmatrix} \Sigma Wk^2 Z \\ \Sigma WkZ \\ \Sigma WZ \end{bmatrix}$$

where $\Sigma$ is a sum over k. Inverting this gives:

$$B = \frac{\Sigma WkZ}{\Sigma Wk^2} \text{ and } \begin{bmatrix} A \\ C \end{bmatrix} = \frac{1}{\Sigma Wk^4 \Sigma W - (\Sigma Wk^2)^2}\begin{bmatrix} \Sigma W & -\Sigma Wk^2 \\ -\Sigma Wk^2 & \Sigma Wk^4 \end{bmatrix} \cdot \begin{bmatrix} \Sigma Wk^2 Z \\ \Sigma WZ \end{bmatrix}$$

Quantities independent of Z can be evaluated beforehand, and stored in a look-up table. Sums over products containing Z still require explicit computation. Once A, B, and C have been computed, the best fit $\tilde{Z}(k)=Ak^2+Bk+C$ can be calculated for $k\in[-24,+24]$, and the following rule can be applied to restore the clipped peak: $Z(k)\leftarrow$extremum $(\tilde{Z}(k),Z(k))$, (i.e., choose the more extreme of the fit and measured values, independently for each k). This will tend to use the fit values across the clipped segment as desired, but revert to the measured values on the tails of the fit window, where the parabolic fit is poor.

Figure 4:
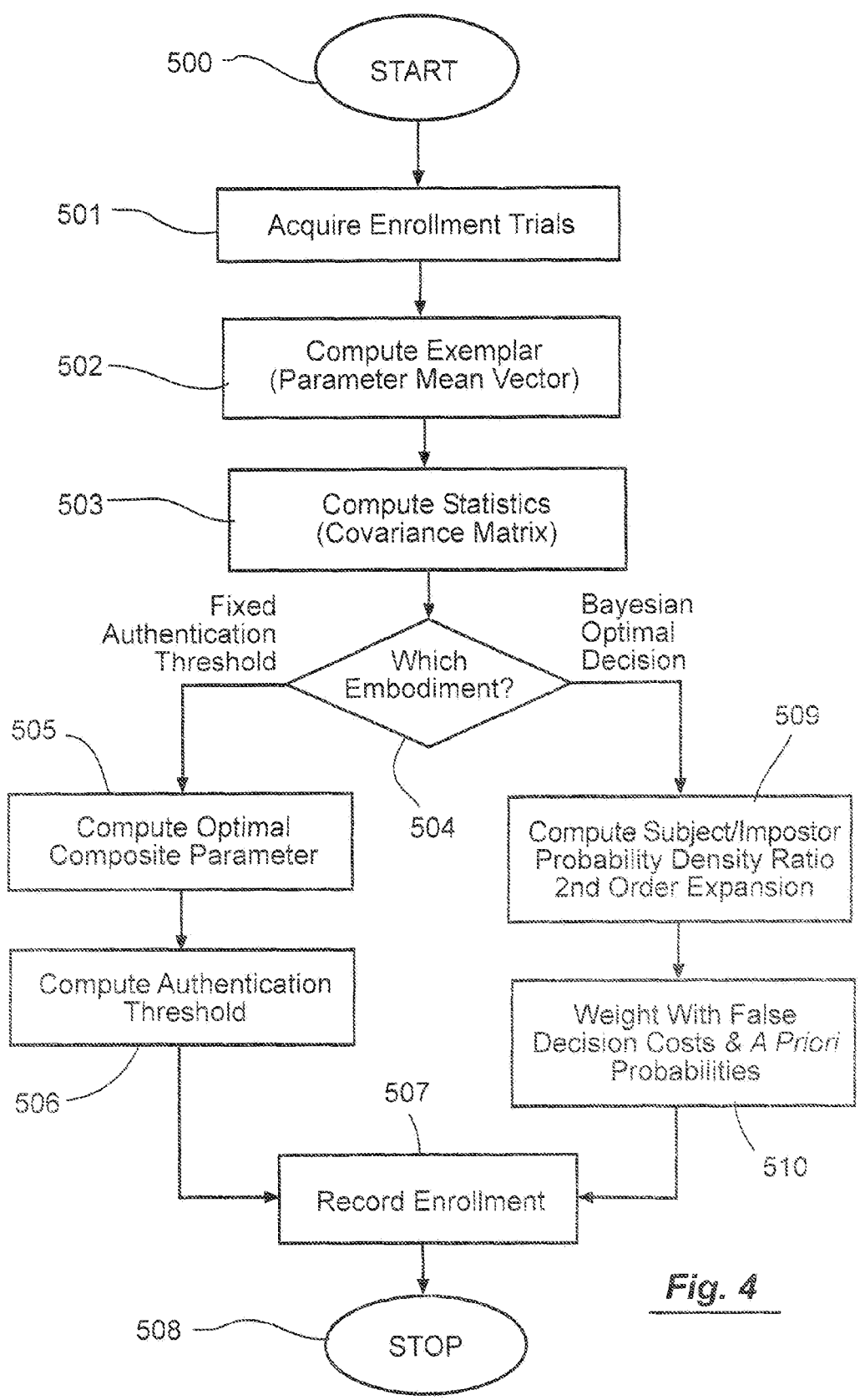
FIG. 4 is a flowchart of the procedure used to enroll a new client.

FIG. 4 shows two embodiments of the procedure used to enroll a new client. This procedure can be used both to establish the client's characteristics as a subject whose identity will be putative in the field, and as a possible impostor for any other client. Block 500 is the start of the procedure. Block 501 acquires a number of trial time periods (e.g., five or seven) by repeatedly calling the appropriate "Acquire Trial" procedure. Block 502 computes the exemplar (i.e., the arithmetic mean over the enrollment trials of any or all of the pulse wave shape vector and possibly other parameters, arranged into a vector) using some or all of the enrollment trials.

In one embodiment of the present invention, only the pulse waveform data from the most consistent trials are averaged to create the exemplar according to a predetermined rule in block 502. For example, the pulse waveform data for the five most-typical trials out of seven total trials can be averaged to create the exemplar. In other words, the two most atypical trials are discarded. In another embodiment, the entire set of enrollment trials for a subject can be rejected as being substandard and the subject is then required to repeat the enrollment trial process. For example, the enrollment trials for a subject can be determined to be substandard if the dynamically-weighted variance of the pulse waveform data exceeds a predetermined threshold.

After block 502 has computed the exemplar, block 503 computes the statistics (i.e., the covariance matrix) of the enrollment trial, as well as the relative weights of the shape vector components. The latter may incorporate either or both of two independent innovations: dynamic weighting, in which portions of the shape vector that are more repeatable from trial to trial are accentuated relative to less repeatable portions; and feature weighting, in which portions of the shape vector that are more specific to the subject are accentuated relative to portions more typical of the population at large.

Block 504 transfers control to one of two blocks, depending on whether the "fixed authentication threshold" or the "Bayesian optimal decision" embodiment of the algorithm is selected. The chief distinction is that the Bayesian embodiment makes use of potential impostor data (i.e., from other clients as potentials impostors for the subject), while the fixed threshold does not. Block 505 finds the principal components of the covariance matrix, and uses the dominant eigenvector (i.e., that with the largest eigenvalue) to linearly combine the parameter vector into a scalar "composite parameter", which is optimal in the sense that the enrollment data has the greatest correlation, and thus the least spread, along the dominant eigenvector. In general, this results in unequal weighting of the parameters in the decision to authenticate or challenge identity. Next, block 506 computes the authentication threshold corresponding to the preset desired true authentication probability (e.g., 7/8). Then, block 507 enrolls the client, and block 508 stops the procedure. On the other bifurcation, block 509 expands the ratio of the subject probability density to the impostor probability density to second order in the deviation from the subject exemplar. Block 510 includes the effects of the generally unequal penalties of false authentication and false challenge, and the a priori probability of attempted deception, which varies among clients. Since the Bayesian optimal decision embodiment uses the entire covariance matrix, it is not necessary or advantageous to define a composite parameter; and since impostor data is incorporated, the true and false authentication probabilities can be traded.

Figure 5:
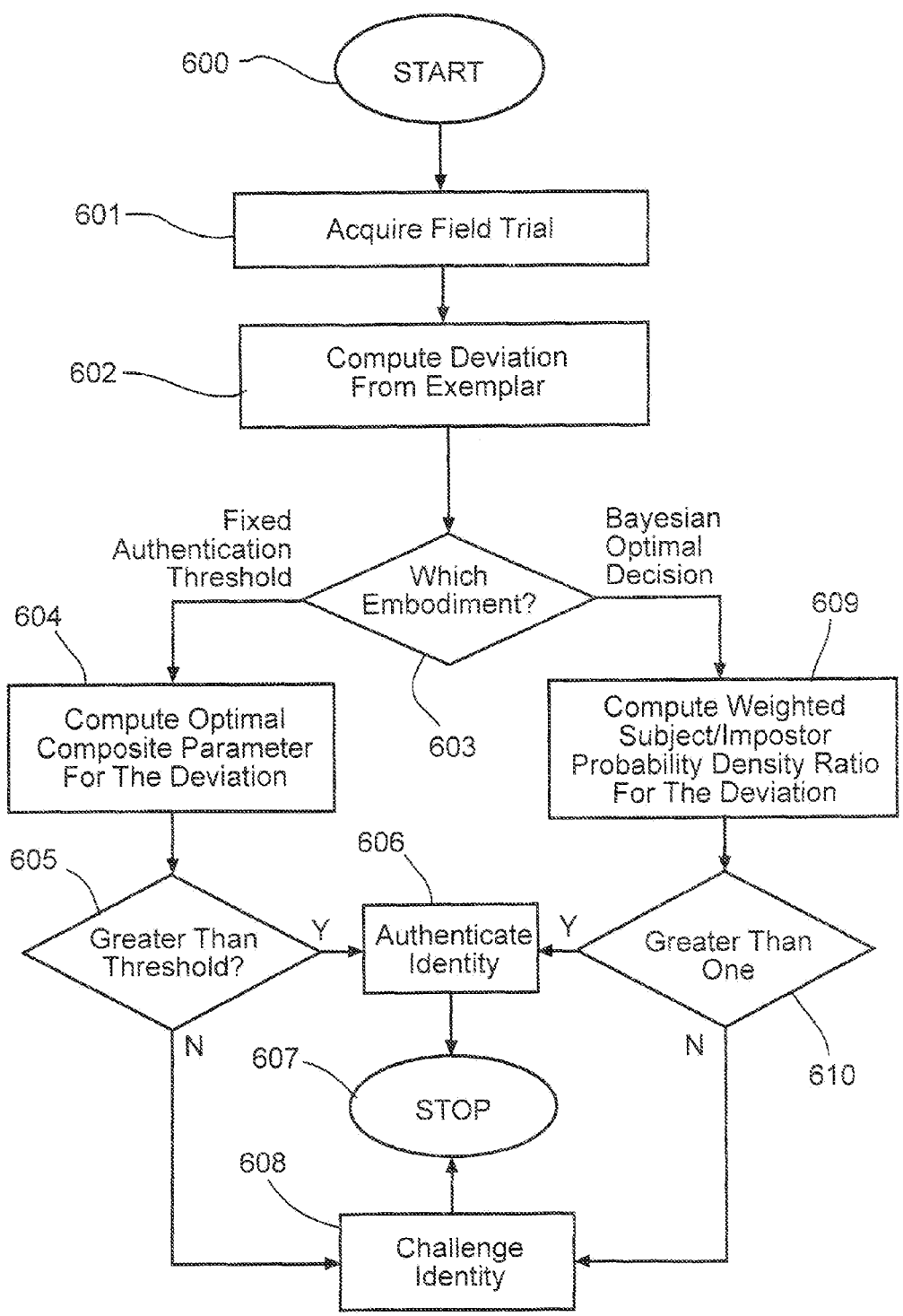
FIG. 5 is a flowchart of the identity authentication mode of the present invention.

FIG. 5 shows how either algorithm embodiment decides whether to authenticate or challenge the subject's identity based on a field trial. Block 600 is the start of the procedure. Block 601 acquires a field trial, and block 602 subtracts the subject exemplar to yield the "deviation", a vector with the same structure as a trial, and optionally applies dynamic or feature weighting to the deviations of the shape vectors. Block 603 transfers control to one of two blocks, depending on whether the "fixed authentication threshold" or the "Bayesian optimal decision" embodiment of the algorithm is selected. Block 604 computes the optimal composite parameter for the deviation, and block 605 compares it to the authentication threshold. If greater, block 606 advises authorities to authenticate the subject's identity, and block 607 stops the procedure. If lesser, block 608 advises authorities to challenge the subject's identity. On the other bifurcation, block 609 computes the ratio of the subject probability density to the impostor probability density to second order in the deviation of the field trial from the subject exemplar, and block 610 compares it to one. If greater than one, block 606 advises authorities to authenticate the subject's identity. If not, block 608 advises authorities to challenge the subject's identity.

As so far described, the algorithm uniformly weights each exemplar shape vector component, placing equal importance on the various features. However, this restriction is unnecessary, and may not be optimal. Some parts of some subjects' exemplars are more characteristic than other parts, so it's reasonable to suppose weighting unusual features more heavily could enhance the distinguishability of subjects.

Figure 6:
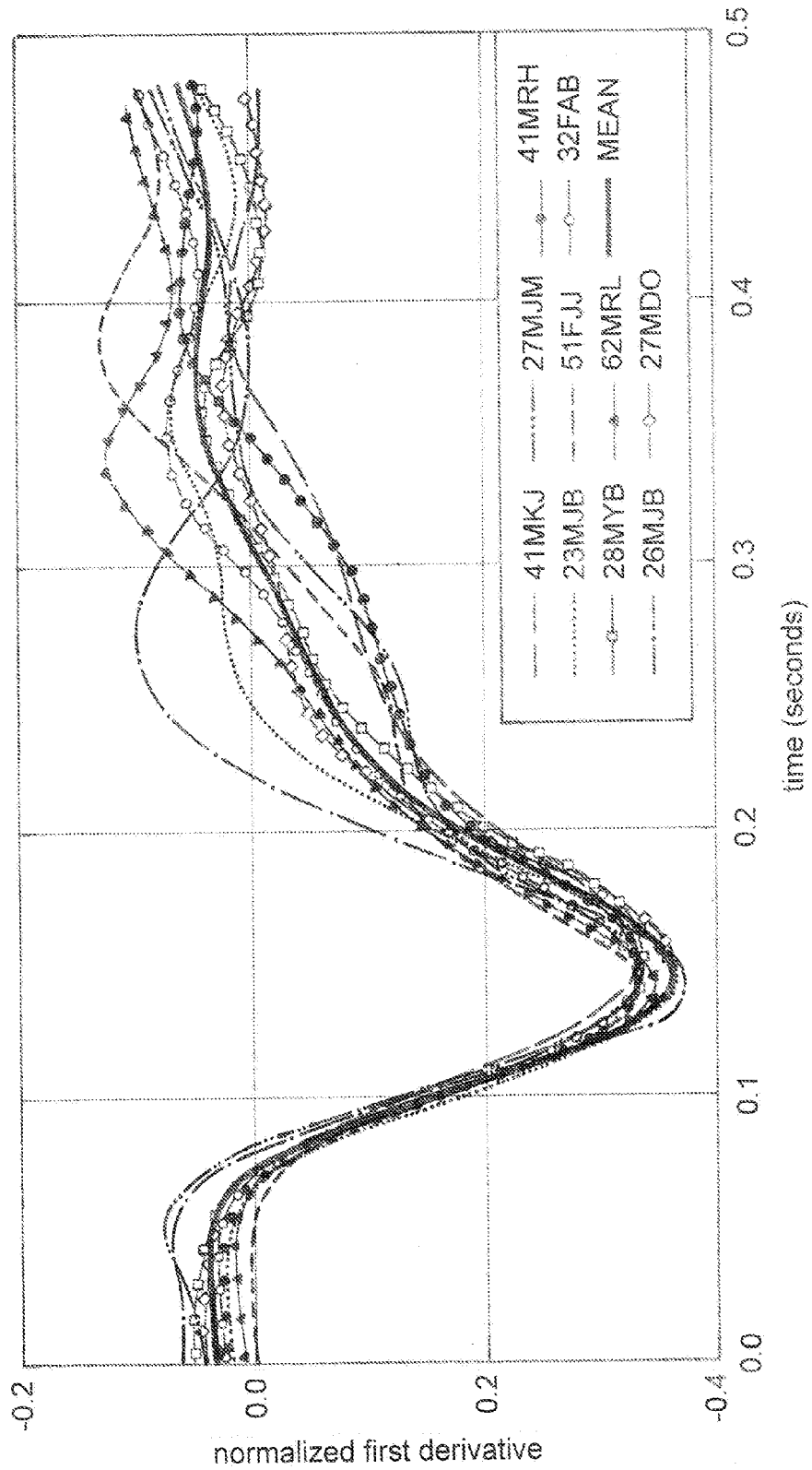
FIG. 6 is a graph showing pulse waveform exemplar shape vectors of the ten subjects of a recent study, along with the mean pulse waveform.

FIG. 6 shows the pulse wave exemplar shape vectors of the ten subjects of a recent study, along with the mean pulse wave shape. Generally, some subjects are more atypical than others, and therefore are more easily identified in the field. Some subjects have features (e.g., subject 26MJB near 0.27 seconds) that are quite distinctive. If these features are weighted more heavily than more typical regions (e.g., subject 26MJB near 0.14 seconds), the subject is more readily recognized when supplying a legitimate field trial, and less easily mimicked by an impostor. An example feature-weighting strategy is to weight each field trial shape vector component proportionally to the square of the deviation of the corresponding subject exemplar component from the mean exemplar component, thus placing greater weight on more unusual features.

One technique for implementing dynamic weighting is to parse the shape vector into segments that are large enough to avoid excessive statistical fluctuations, yet small enough to provide resolution of the varying character across the vector (e.g., a 100-component pulse waveform vector into 20 five-component segments), and assign a different weight to each segment based on its fluctuations. An example dynamic-weighting strategy is to weight each field trial shape vector segment proportionally to the reciprocal of the segment's variance (i.e., the sum over enrollment trials and segment components of the squared deviation of the enrollment trial component from the exemplar component), thus placing greater weight on more repeatable segments.

One technique for implementing feature weighting is to raise each shape vector component probability to a different power greater or less than unity, according to how much the exemplar shape deviates from the average subject at that point. The feature weighting function can be expressed as a vector of the same dimensionality as the shape itself, consisting of components whose average is unity (equal weighting is encompassed as the special case where all components are one). This approach keeps the rest of the algorithm unaffected by whether feature weighting is selected or disabled. In general, the feature weighting vector is different for each client.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A method for biometric identity confirmation of a subject having a pulse, said method comprising:
   during an initial training mode, acquiring pulse waveform data from a known subject;
   generating and storing subject characterization data for the known subject based at least in part on an exemplar created by synchronous averaging of pulse waveform data over multiple pulse cycles, wherein said synchronous averaging of pulse waveform data includes:
   (a) identifying trigger candidates for a start point of each pulse cycle;
   (b) analyzing a time delay between trigger candidates to discard false trigger candidates and identify true trigger candidates; and
   (c) synchronously averaging the pulse waveform data for each pulse cycle using the true trigger candidates as start points for each pulse cycle; and
   during a subsequent identity authentication mode, acquiring pulse waveform data from a test subject, and analyzing the pulse waveform data with the subject characterization data for the known subject to confirm whether the identity of the test subject matches the known subject.

2. The method of claim 1 wherein the trigger candidates are derived at least in part from a second derivative of the pulse waveform data with respect to time.

3. The method of claim 1 wherein the step of acquiring and analyzing pulse waveform data for a test subject further comprises:
   acquiring pulse waveform data from the test subject over multiple pulse cycles;
   identifying trigger candidates for the start point of each pulse cycle:
   analyzing the time delay between trigger candidates to discard false trigger candidates and identify true trigger candidates; and
   synchronously averaging the pulse waveform data for each pulse cycle using the true trigger candidates as the start points for each pulse cycle.

4. The method of claim 1 wherein the step of generating subject characterization data further comprises:
   computing an exemplar in the form of a parameter vector from the pulse waveform data for the known subject;
   computing a covariance matrix from the pulse wave data for the known subject;
   computing an optimal composite parameter from the covariance matrix and parameter vector that is characteristic of the known subject; and
   computing an authentication threshold corresponding to a desired true authentication probability for the known subject.

5. The method of claim 1 wherein the step of analyzing the pulse waveform data with the subject characterization data for the known subject to confirm whether the identity of the test subject matches the known subject further comprises:
   computing a deviation of the pulse waveform data for the test subject from the exemplar for the known subject:
   computing an optimal composite parameter from the deviation; and
   confirming the identity of the test subject matches the known subject if optimal composite parameter is greater than the authentication threshold for the known subject.

6. The method of claim 1 wherein the step of generating subject characterization data further comprises:
   computing an exemplar in the form of a parameter vector from the pulse waveform data for the known subject;
   computing a covariance matrix from the pulse waveform data for the known subject; and
   computing a probability distribution ratio of a weighted subject/impostor probability density by a Bayesian optimal decision analysis of the parameter vector, covariance matrix, and data from other subjects as potential impostors for the known subject.

7. The method of claim 1 wherein the step of analyzing the pulse waveform data with the subject characterization data for the known subject to confirm whether the identity of the test subject matches the known subject further comprises:

computing a deviation of the pulse waveform data for the test subject from the exemplar for the known subject;

computing a weighted subject/impostor probability density ratio for the deviation; and confirming the identity of the test subject matches the known subject if the weighted subject/impostor probability density ratio is greater than one.

8. The method of claim 1 wherein the step of generating subject characterization data further comprises weighting portions of the exemplar selected based on their repeatability observed during the initial training mode.

9. The method of claim 1 wherein the step of generating subject characterization data further comprises weighting portions of the exemplar selected to distinguish characteristic features of the known subject observed during the initial training mode.

10. The method of claim 1 wherein the initial training mode acquires a plurality of sets of pulse waveform data over a plurality of trials, and wherein the step of synchronous averaging includes only the pulse waveform data from the most consistent trials.

11. The method of claim 1 wherein the initial training mode acquires a plurality of sets of pulse waveform data over a plurality of trials, and wherein the trials are rejected if the variance of the pulse waveform data exceeds a predetermined threshold.

* * * * *